United States Patent [19]

Rash

[11] 4,231,367

[45] Nov. 4, 1980

[54] INFUSION CATHETER ASSEMBLY

[75] Inventor: Douglas L. Rash, Orchard Park, N.Y.

[73] Assignee: Viggo AB, Sweden

[21] Appl. No.: 843,594

[22] Filed: Oct. 19, 1977

[30] Foreign Application Priority Data

Oct. 26, 1976 [SE] Sweden ............................. 7611858

[51] Int. Cl.² ............................................. A61M 5/00
[52] U.S. Cl. ................................ 128/214.4; 128/221; 128/DIG. 16
[58] Field of Search ................. 128/214.4, 214.2, 215, 128/218 D, 220, 221, 2 F, 348–351, 347; 27/24 A

[56] References Cited

U.S. PATENT DOCUMENTS

| 2,234,686 | 3/1941 | Walter ............................. 27/24 A X |
| 3,727,613 | 4/1973 | Sorenson et al. .................. 128/214.4 |
| 3,890,972 | 6/1975 | Standley et al. ..................... 128/220 |
| 3,923,066 | 12/1975 | Francisoud et al. ................. 128/348 |
| 4,079,738 | 3/1978 | Dunn et al. ....................... 128/214.4 |
| 4,123,091 | 10/1978 | Cosentino et al. .......... 128/214 R X |

Primary Examiner—Dalton L. Truluck
Attorney, Agent, or Firm—Brumbaugh, Graves, Donohue & Raymond

[57] ABSTRACT

An infusion catheter assembly, which includes a catheter unit and an insertion needle unit, is provided with fins extending from the head of the insertion needle unit. The fins may be gripped by the fingers and pivoted inward to firmly engage the catheter unit during insertion of the catheter unit into a vein.

8 Claims, 7 Drawing Figures

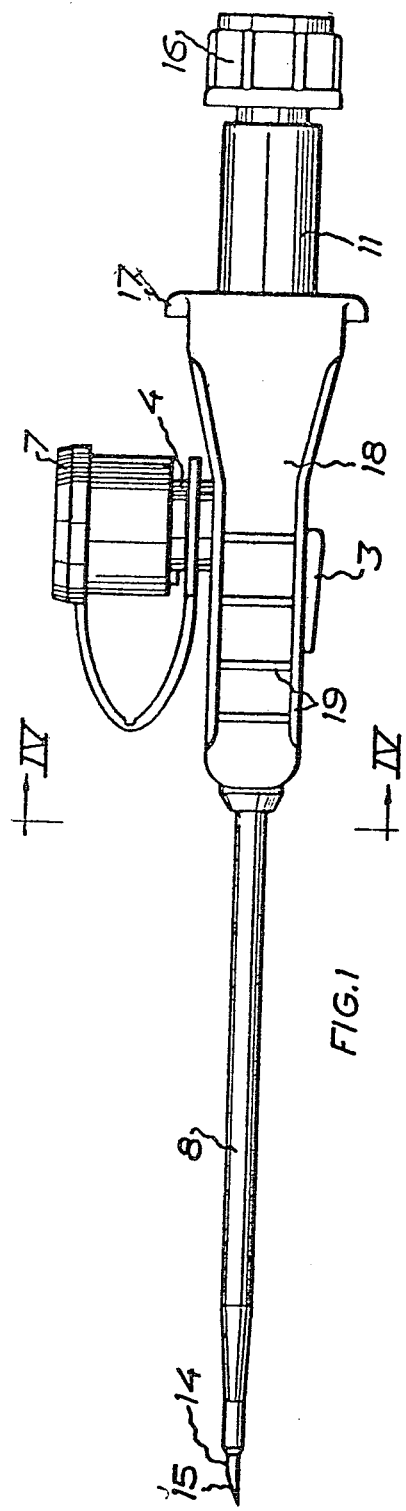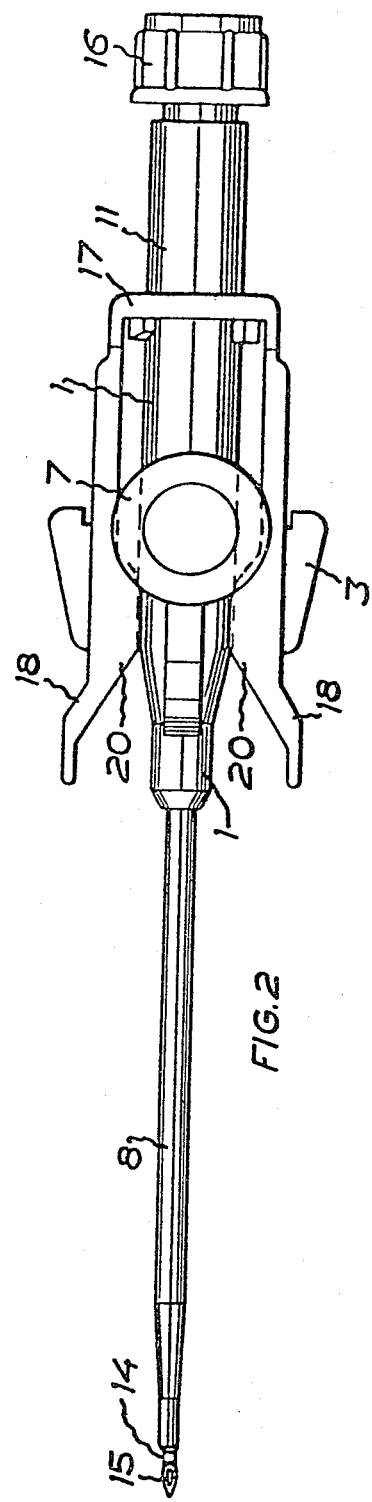

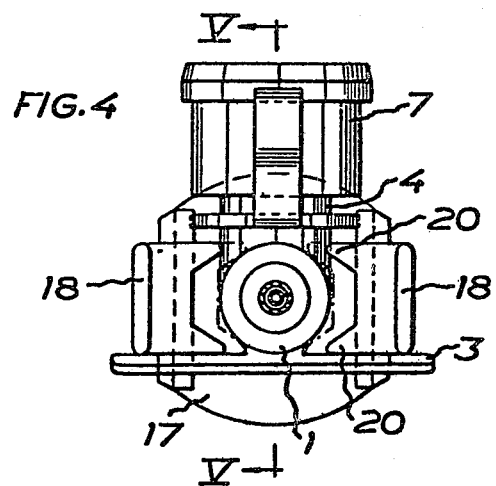
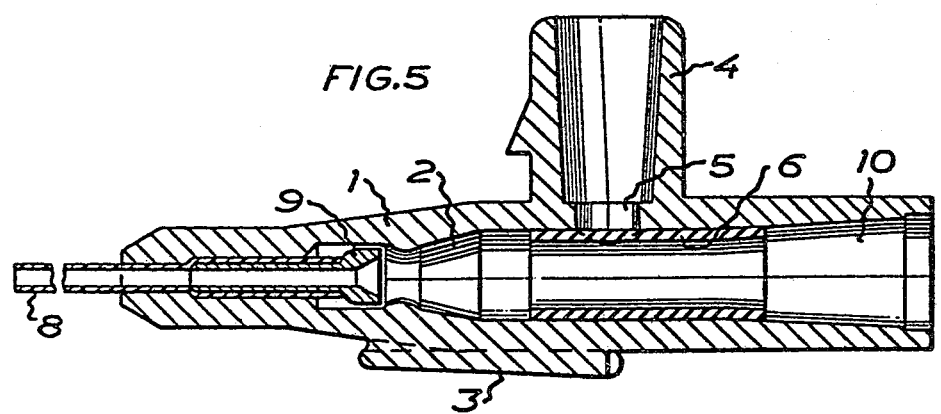

INFUSION CATHETER ASSEMBLY

BACKGROUND OF THE INVENTION

This invention relates to infusion catheter devices and particularly to such devices in which a catheter unit is assembled with an insertion needle unit for insertion into a vein, and following insertion the needle is removed from the catheter unit.

Infusion catheter assemblies of the type to which the invention relates, such as that disclosed in Swedish Pat. No. 355,946 are relatively difficult to insert, because the assembly is difficult to properly grasp. Further, such catheter assemblies must be gripped by the user at a position on the unit which is considerably removed from the tip of the insertion needle, thereby making accurate control of the tip difficult.

It is therefore an object of the invention to provide a new and improved infusion catheter assembly which may be more easily gripped by the user.

It is a further object of the invention to provide such an assembly which may be gripped in a region which is relatively close to the tip of the insertion needle.

SUMMARY OF THE INVENTION

In accordance with the invention, there is provided an insertion needle unit for use in inserting a catheter unit having a catheter tube mounted to one end of an elongated housing unit, and a coupling at the other end of the housing unit. The insertion needle unit includes a head adapted to engage the coupling, an insertion needle extending from the head and adapted for insertion through the catheter tube, and a pair of digitally grippable fins extending from the head in the direction of the needle on opposite sides of the needle. The fins are made of resilient material and are deflectable by finger pressure to bear against the housing unit when the needle is inserted through the catheter tube.

The insertion needle unit is usully provided as part of an infusion catheter assembly, which includes a catheter unit. The assembly may include engagement means for engaging the fins and the housing unit when the fins are deflected. The engagement means may be a transverse projection on the housing unit and mutually projecting lugs on the fins. In a preferred embodiment, the engaging means are designed to cause the catheter unit to be properly seated in position on the insertion needle unit when the fins engage the housing unit.

For a better understanding of the present invention, together with other and further embodiments, reference is made to the following description, taken in conjunction with the accompanying drawings, and its scope will be pointed out in the appended claims.

BRIEF DESCRIPTION OF THE DRAWINGS

FIG. 1 is a side view of an infusion catheter assembly in accordance with the present invention.

FIG. 2 is a top view of the FIG. 1 catheter assembly.

FIG. 4 is a transverse cross-sectional view of the FIG. 1 assembly.

FIG. 5 is a longitudinal cross-sectional view of the catheter unit of the FIG. 1 assembly.

DESCRIPTION OF THE INVENTION

Figure 3:
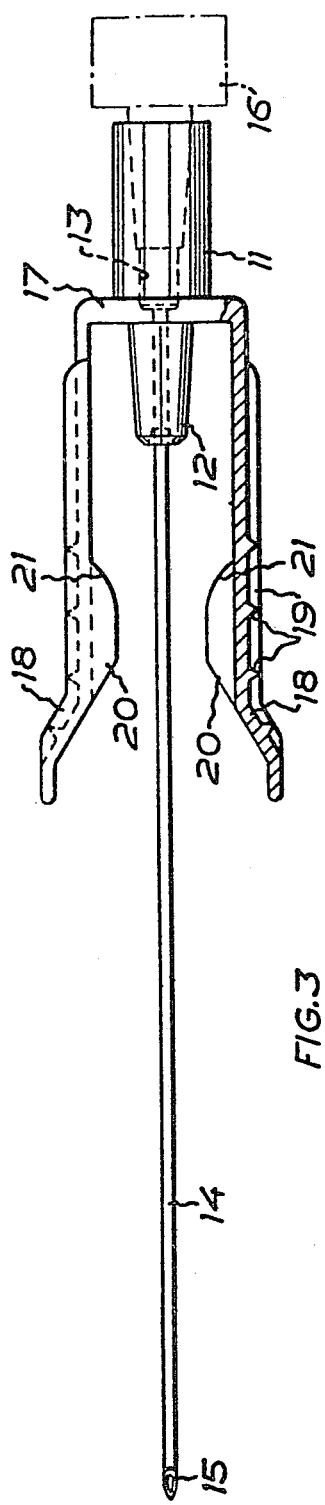
FIG. 3 is a top view of the insertion needle unit of the FIG. 1 assembly.

Referring generally to FIGS. 1 through 5, there is shown a catheter assembly which consists of a catheter unit and an insertion needle unit. The insertion needle unit alone is shown in FIG. 3, and a cross-sectional view of the catheter unit alone is shown in FIG. 5.

The catheter unit includes elongated housing unit 1 with a passage 2 extending longitudinally between the two ends. One end 10 of the passage is adapted to receive a coupling mechanism so that the catheter unit may be connected to a tube or injection syringe. A flexible catheter tube 8 is mounted to the other end of the housing and communicates with passage 2. A bushing 9 retains catheter tube 8 in the end of housing unit 1.

In the particular embodiment illustrated, the housing unit 1 is provided with a connecting sleeve 4 which communicates with passage 2 through orifice 5. A section of hose 6 serves as a non-return valve for orifice 5. Connecting sleeve 4 may be closed by means of a cap 7. It should be understood that connecting sleeve 4, orifice 5, and valve 6 have no particular bearing on the present invention, but the exterior surfaces of connecting sleeve 4 may be conveniently used in one embodiment of the present invention as will be explained.

The exterior of housing 1 is provided with a base plate 3, so that the catheter unit can be easily attached to a patient's skin by tape after insertion of tube 8 into a vein.

The insertion needle unit, illustrated alone in FIG. 3, includes a head 11 which is provided with a conical portion 12 which engages the coupling end 10 of housing 1 when needle 14 is inserted through catheter tube 8. An axial channel 13 in head 11 communicates with the interior of hollow needle 14. Passage 13 may be closed by the use of a plug 16, which is shown in FIGS. 1 and 2. The length of needle 14 is selected so that the tip 15 will protrude slightly from tube 8 when tapered portion 12 is seated in the coupling end 10 of housing unit 1. Head 11 is provided with a flange 17 which is integrally connected with fins 18 as a single U-shaped member. Fins 18 are made of resilient material, such as flexible plastic or metal, and extend in a longitudinal direction substantially parallel to needle 14. When the insertion needle unit is mounted to the catheter unit, as shown in FIGS. 1 and 2, fins 18 extend along the exterior of housing unit 1. The outwardly facing surfaces of fins 18 are provided with ridges 19 to facilitate gripping of the fins by the fingers. The inside portions of fins 18 are provided with lugs 20 which engage the housing unit of the syringe.

Lugs 20 are preferably arranged forward of the center of connecting sleeve 4 housing 1 so that upon gripping of the fins with the fingers and squeezing of the fins, the inclined edges 21 of lugs 20 engage sleeve 4 and cause the catheter unit to be properly seated in position and held firmly on the insertion needle unit. In the event the catheter unit is displaced axially or rotated on the insertion needle unit prior to use, the action of lugs 20 on sleeve 4 will cause a rotational centering and longitudinal seating of the catheter unit on the insertion unit.

From the foregoing description, it will become evident that the catheter assembly in accordance with the invention is adapted for easy and convenient use by medical personnel. When the catheter is to be inserted, the user grasps fins 18 which causes the catheter unit to be centered, securely seated, and firmly held on the insertion needle. The needle and catheter may then be inserted through the skin and into a vein. Following puncture of the vein by the needle, the user may move the catheter unit forward on the insertion needle, in the process of "hooding" the insertion needle point, and then guide the catheter end with the hooded needle into the desired position in the vein. Following insertion, the insertion needle is usually withdrawn from the catheter tube and housing unit and the catheter may be used in the normal manner by connecting a tube or syringe in coupling 10. In addition to securely holding the catheter unit on the insertion needle during insertion, the assembly of the invention enables the practitioner to grasp the assembly at a position which is relatively close to the tip of the insertion needle. This grasping position permits easier and more precise control of the insertion of the catheter. After insertion of the catheter, the housing 1 is taped to the patient's skin by use of base plate 3, and a connection piece for a tube or injection syringe is coupled at the end 10 of housing 1. Connecting sleeve 4 may also be provided with a connecting piece so that injection of medication may be provided through the catheter during intravenous infusion of other liquids through the connection in housing end 10.

It will be evident that the existence of a passage through sleeve 4 has no particular bearing on the engagement of the outside of sleeve 4 with lugs 20 on fins 18. Consequently, in a catheter unit which is not provided with an additional connection sleeve 4, a simple molded projection on housing unit 1 may be provided for engaging lugs 20 on fins 18.

Another possible arrangement for the engagement between fins 18 and housing unit 1 is the provision of lugs or other members on fins 18 which are adapted to engage a tapered portion 24 on the outside of housing 1. By engaging the tapered portion 24, the lugs can be used to properly seat the catheter unit on the insertion needle.

Figure 6:
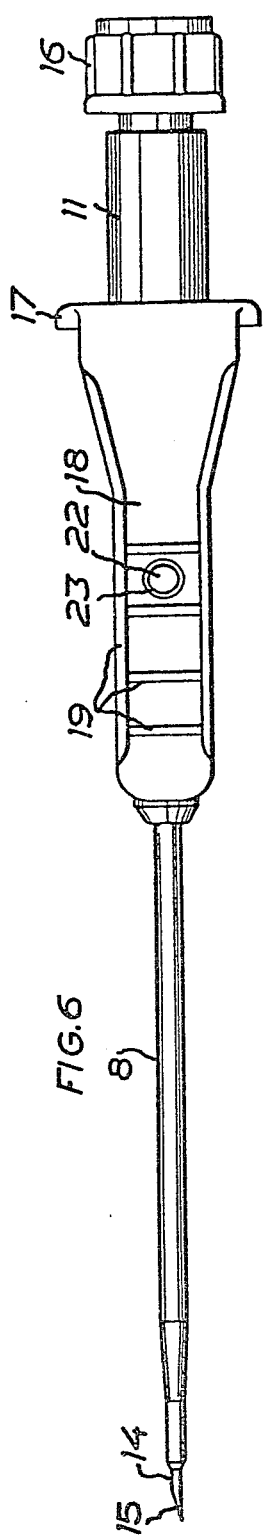
FIG. 6 is a side view of an alternate embodiment of an infusion catheter assembly in accordance with the present invention.
Figure 7:
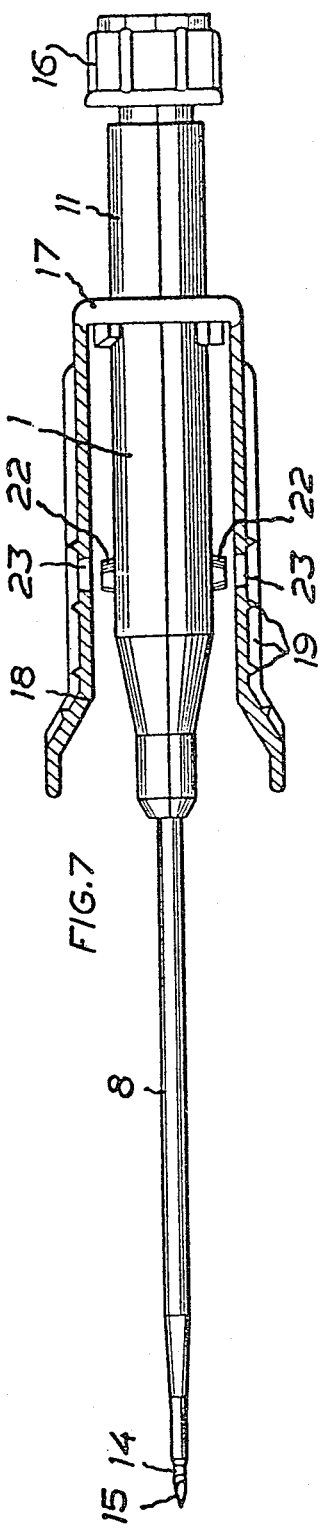
FIG. 7 is a partially cross-sectional top view of the FIG. 6 assembly.

FIGS. 6 and 7 illustrate still another embodiment of the invention wherein the housing unit is not provided with a base plate, and wherein there is no connecting sleeve on the housing. As illustrated in those FIGS., there are provided projections 22 on the outside of housing 1 which engage holes 23 on fins 18. Projections 22 and holes 23 are tapered so that the catheter unit is properly seated and located by the engagement of projection 22 with holes 23. It will be recognized that projections may likewise be provided on the fins and recesses provided on the housing for mutual engagement.

While there have been described what are believed to be the preferred embodiments of the invention, those skilled in the art will recognize that other and further modifications may be made thereto without departing from the spirit of the invention, and it is intended to claim all such embodiments as fall within the true scope of the invention.

I claim:

1. An infusion catheter assembly comprising a catheter unit and an insertion needle unit, said catheter unit comprising an elongated housing unit having a longitudinal passage and adapted to receive a coupling device at one end, and a flexible catheter tube, having a free end mounted to the other end of said housing in communication with said passage, said insertion needle unit comprising a head engaging said coupling end of said housing unit, a needle extending from said head through said passage and catheter tube and protruding from said free end of said tube, and a pair of digitally grippable fins projecting from said head and extending along opposite sides of said housing in the elongated direction and in the same direction from said head as said needle, said fins being fabricated of resilient material and capable of being pressed by finger pressure against said housing unit.

2. An infusion catheter assembly as specified in claim 1 wherein said housing unit and said fins are provided with engagement means for engaging said fins and said housing unit when said fins are deflected.

3. An infusion catheter assembly as specified in claim 2 wherein said engagement means comprises a transverse projection on said housing and mutually projecting lugs on said fins.

4. An infusion catheter assembly as specified in claim 3 wherein said engagement means is arranged to cause said housing unit to seat on said head when said fins are deflected.

5. An infusion catheter assembly as specified in claim 2 wherein said engagement means is arranged to prevent axial or rotational movement of said catheter unit with respect to said insertion needle unit when engaged.

6. An infusion catheter assembly as specified in claim 2 wherein said engagement means comprise mutually cooperating projections and holes on said housing unit and said fins.

7. An infusion catheter assembly as specified in claim 1 wherein said insertion needle unit includes a flange mounted to said head and wherein said fins are attached to said flange.

8. An infusion catheter assembly as specified in claim 7 wherein said flange and said fins are formed as a single U-shaped member attached to said head.

* * * * *

UNITED STATES PATENT AND TRADEMARK OFFICE
CERTIFICATE OF CORRECTION

PATENT NO. : 4,231,367
DATED : November 4, 1980
INVENTOR(S) : Douglas L. Rash

It is certified that error appears in the above-identified patent and that said Letters Patent are hereby corrected as shown below:

Col. 2, line 55, after "4" insert --of--;

Col. 4, line 34, "3" should read --2--.

Signed and Sealed this

Thirty-first Day of March 1981

[SEAL]

Attest:

RENE D. TEGTMEYER

Attesting Officer     Acting Commissioner of Patents and Trademarks